(12) United States Patent
Kawinski et al.

(10) Patent No.: US 6,475,389 B2
(45) Date of Patent: Nov. 5, 2002

(54) METHOD FOR DETECTION OF PROSTATE SPECIFIC MEMBRANE ANTIGEN IN SERUM

(75) Inventors: Elzbieta Kawinski, Orchard Park, NY (US); Kailash C. Chadha, Williamsville, NY (US)

(73) Assignee: Health Research, Inc., Buffalo, NY (US)

( * ) Notice: Subject to any disclaimer, the term of this patent is extended or adjusted under 35 U.S.C. 154(b) by 17 days.

(21) Appl. No.: 09/851,263

(22) Filed: May 8, 2001

(65) Prior Publication Data

US 2002/0049712 A1 Apr. 25, 2002

Related U.S. Application Data

(63) Continuation-in-part of application No. 09/624,692, filed on Jul. 24, 2000, now Pat. No. 6,379,550.

(51) Int. Cl.$^7$ .............................................. G01N 33/574
(52) U.S. Cl. .................... 210/635; 210/656; 210/198.2; 435/7.1; 435/7.23; 530/388.8
(58) Field of Search ..................... 435/7.1, 7.2, 7.23, 435/326, 344, 344.1; 530/387.9, 388.8, 387.1, 388.2, 388.85; 210/635, 656, 659, 198.2; 436/518

(56) References Cited

U.S. PATENT DOCUMENTS

| | | | | |
|---|---|---|---|---|
| 5,162,504 A | | 11/1992 | Horoszewicz | 530/388.2 |
| 5,489,525 A | * | 2/1996 | Pastan | 435/7.23 |
| 5,538,866 A | * | 7/1996 | Israeli | 435/69.3 |
| 5,962,237 A | * | 10/1999 | Ts'O | 435/7.23 |
| 5,962,274 A | * | 10/1999 | Parks | 435/91.1 |
| 6,107,090 A | * | 8/2000 | Bander | 530/388.8 |
| 6,136,311 A | * | 10/2000 | Bander | 530/388.8 |
| 6,150,508 A | * | 11/2000 | Murphy | 530/388.8 |
| 6,200,765 B1 | * | 3/2001 | Murphy | 435/7.23 |
| 6,365,362 B1 | * | 4/2002 | Terstappen | 435/7.23 |
| 6,379,550 B1 | * | 4/2002 | Chadha | 210/635 |
| 6,383,759 B1 | * | 5/2002 | Murphy | 435/7.1 |

OTHER PUBLICATIONS

Beckett, et al., Prostate–specific membrane antigen levels in sera from healthy men and patients with benign prostate hyperplasia or prostate cancer, Clin Cancer Res, vol. 5, pp 4034–4040, 1999.

Bostwick, et al., Prostate–specific membrane antigen expression in prostatic intraepithelial neoplasia and adenocarcinoma: A study of 184 cases, Cancer, vol. 82, pp 2256–2261, 1998.

(List continued on next page.)

Primary Examiner—Ernest G. Therkorn
(74) Attorney, Agent, or Firm—Michael L. Dunn

(57) ABSTRACT

A method for detecting prostate specific membrane antigen (PSMA) in serum by immunoassay including the steps of capturing PSMA from serum using a PSMA antibody and detecting the captured PSMA with an anti-$\alpha_1$-antichymotrypsin antibody. In a preferred embodiment, PSMA is captured using a PSMA antibody by diluting the PSMA antibody, coating a surface such as the surface of wells in a microtiter plate, with the resulting solution, blocking non-specific sites on the surface with albumin, diluting the serum with a blocking buffer and applying a diluted sample to the surface to capture PSMA. A preferred embodiment for detecting captured PSMA, includes the steps of removing non-captured material by washing the surface, applying anti-$\alpha_1$antichymotrypsin antibody diluted in a blocking solution such as albumin solution and detecting bound PSMA using peroxidase labeled anti-rabbit IgG and OPD substrate.

9 Claims, 7 Drawing Sheets

OTHER PUBLICATIONS

Grasso, et al., Combined nested RT–PCR assay for prostate–specific antigen and prostate–specific membrane antigen in prostate cancer patients: correlation with pathological stage, Cancer Research, vol. 58, pp 1456–1459, 1998.

Horoszewicz, et al., LNCaP model of prostatic carcinoma, Cancer Res, vol. 43, pp 1809–1818, 1983.

Horoszewicz, et al., Monoclonal antibodies to a new antigenic marker in epithelial prostatic cells and serum of prostatic cancer patients, Anticancer Res, vol. 7, pp 927–936, 1987.

Israeli, et al., Molecular cloning of a complimentary DNA encoding of prostate–specific membrane antigen, Cancer Res, vol. 53, pp 227–230, 1993.

Polascik, et al., Prostate–specific antigen: A decade of discovery–what we have learned and where we are going, J. Urol, vol. 162, pp 293–306, 1999.

Rochon, et al., Western–blot assay for prostate–specific membrane antigen in serum of prostate cancer patients, Prostate, vol. 25, pp 219–223, 1994.

Silver, et al., Prostate–specific membrane antigen expression in normal and malignant human tissues, Clin Cancer Res, vol. 3, pp 81–85, 1997.

Sokoloff, et al., A dual–monoclonal sandwish assay for prostate–specific membrane antigen: Levels in tissues, seminal fluid and urine, Prostate, vol. 43, pp 150–157, 2000.

Sweat, et al., Prosate–specific membrane antigen expression is greatest in prostate adenocarcinoma and lymph node metastasis, Urology, vol. 52, pp 637–640, 1998.

Troyer, et al., Detection and characterization of the prostate–specific membrane antigen (PSMA) in tissue extracts and body fluids, Int. J. Cancer, vol. 62, pp 552–558, 1995.

Abstract of Wright, et al., Expression of prostate–specific membrane antigen (PSMA) in normal, benign, and malignant prostate tissues, Urol Oncol, vol. 1, pp 18–28, 1995.

Leinonen, et al., Double–label time–resolved immunofluorometric assay of prostat–specific antigen and of its complex with alpha–1–antichymotrypsin, Clinical Chemistry, vol. 39, No. 10, 1993, pp 2098–2103.

Murphy, et al., Measurement of prostat–specific membrant antigen in the serum with a new antibody, The Prostate, vol. 28, No. 4, 1996, pp 266–271.

* cited by examiner kDa

←250

←98

←64

←30

A  B

Fig. 1 kDa

METHOD FOR DETECTION OF PROSTATE SPECIFIC MEMBRANE ANTIGEN IN SERUM

This is a Continuation-in-Part of U.S. application Ser. No. 09/624,692, filed Jul. 24, 2000, now U.S. Pat. No. 6,379,550.

BACKGROUND OF THE INVENTION

It is becoming increasingly evident that the monitoring of prostate-specific membrane antigens (PSMA) is desirable for the detection and management of prostate cancer.

Prostate cancer is the most common cancer in males in the United States. The efficiency of early detection of prostate cancer has increased with a serum test for the prostate-specific antigen (PSA). However, PSA is neither tissue-specific nor disease-specific. Many other conditions of the prostate gland, some of them being benign, can also result in abnormal elevation of PSA level in the serum (Polascik, et al., Prostate-specific antigen: A decade of discovery—what we have learned and where we are going, J. Urol, vol 162, pp 293–306, 1999).

Prostate-specific membrane antigen (PSMA) is a transmembrane glycoprotein with both intra and extracellular domains, and is highly specific for the prostate tissue (Israeli, et al., Molecular cloning of a complimentary DNA encoding of prostate-specific membrane antigen, Cancer Res, vol 53, pp 227–230, 1993). PSMA is expressed in benign and malignant prostatic epithelium and can be detected immunohistochemically (Horoszewicz, et al. Monoclonal antibodies to a new antigenic marker in epithelial prostatic cells and serum of prostatic cancer patients, Anticancer Res, vol 7, pp 927–936, 1987; Silver, et al., Prostate-specific membrane antigen expression in normal and malignant human tissues, Clin Cancer Res, vol 3, pp 81–85, 1997; Wright, et al., Expression of prostate-specific membrane antigen (PSMA) in normal, benign, and malignant prostate tissues, Urol Oncol, vol 1, pp 18–28, 1995; Bostwick, et al., Prostate-specific membrane antigen expression in prostatic intraepithelial neoplasia and adenocarcinoma: A study of 184 cases, Cancer, vol 82, pp 2256–2261, 1998; and Sweat, et al., Prostate-specific membrane antigen expression is greatest in prostate adenocarcinoma and lymph node metastasis, Urology, vol 52, pp 637–640, 1998). PSMA serum levels have been proposed to be of prognostic significance in prostate cancer patients with advanced disease, see e.g. Grasso, et al., Combined nested RT-PCR assay for prostate-specific antigen and prostate-specific membrane antigen in prostate cancer patients: correlation with pathological stage, Cancer Research vol 58, pp 1456–1459, 1998.

Attempts to reliably detect PSMA in serum have not been successful and currently, there is no routine methodology available to monitor PSMA levels in the sera of prostate cancer patients.

PSMA expression in human prostate tissue was documented for the first time by immunohistochemical staining using 7E11.C5-antibody (Horoszewicz, et al, supra). The 7E11.C5 monoclonal antibody that was raised against human prostate cancer cells (LNCaP) is known to bind to intracellular epitope of PSMA near the amino terminus. An isotope conjugated form of 7E11.C5, designated CYT-356, has been utilized for the identification of local and distant prostate cancer metastasis and recurrence. 7E11.C5 antibody is deposited with the American Type Culture Collection at Rockville, Md., USA having ATCC access number HB10494. The PSMA immunoreactivity was found to be greater in high-grade prostate tumors as compared to benign prostatic hyperplasia (BPH) and normal cells (Horoszewicz, et al. supra; Silver, et al., supra; Wright, et al, supra; Bostwick, et al, supra; and Sweat, et al., supra). However, among 33 cell lines tested by Horoszewicz, et al., supra, PSMA immunoreactivity was detected only in lymph node carcinoma of prostate (LNCaP) cells. In 1997, the US Food and Drug Administration approved the use of radioimmunoconjugate form of 7E11.C5 (CYT 356) for the detection of localized prostate cancer.

Attempts made to measure PSMA in the serum of patients having prostate cancer by Western-blot analysis have not been conclusive, (Troyer, et al., Detection and characterization of the prostate-specific membrane antigen (PSMA) in tissue extracts and body fluids, Int. J. Cancer, vol 62, pp 552–558, 1995; Rochon, et al., Western-blot assay for prostate-specific membrane antigen in serum of prostate cancer patients, Prostate, vol 25, pp 219–223, 1994; and Beckett, et al., Prostate-specific membrane antigen levels in sera from healthy men and patients with benign prostate hyperplasia or prostate cancer, Clin Cancer Res, vol 5, pp 4034–4040, 1999). It has been reported that Western-blot analysis can show an increase in serum PSMA levels in patients with later stage $C_1$, $D_1$ and $D_2$ prostate cancer as compared to normal (Rochon, et al. supra). On the other hand, Troyer, et al. supra reported that they were unable to detect PSMA in the serum of prostate cancer patients. Beckett, et al. supra reported that they were able to detect PSMA in the serum, but they were unable to distinguish between early and late stage of the disease.

Prior to the present invention, attempts to use the simpler ELISA to detect prostate cancer have not been successful. In "competitive-inhibition" ELISA, PSMA was previously detected in 46% of sera from prostate cancer patients and none in BPH or normal individuals (Horoszewicz, et al. supra). This is clearly insufficient reliability for a determinative test.

In our prior studies, it has been shown that PSA has strong affinity for Thiophilic gels (1S, 2S and 3S) as described in co-pending U.S. patent application Ser. No. 09/624,692, filed Jul. 24, 2000. Recently, we have made an observation that PSMA also has a strong affinity for T-gels. Briefly, a T-gel slurry is packed in a column (0.5×5 cm) and equilibrated with 25 mM Hepes buffer, containing 1M sodium sulfate, pH 7.0. A source of PSMA, e.g. solubilized cell extract from LNCaP cells ($5 \times 10^7$ cells/ml) or human serum (400 μl) is reconstituted with column equilibrating buffer and applied to the column. The column is then washed with approximately 10 void volumes of column equilibrating buffer and the bound proteins are eluted with 25 mM Hepes buffer, pH 7.0. The presence of PSMA in various column fractions is then detected by SDS-PAGE and Western-blot analysis using a monoclonal anti PSMA antibody, such as 7E11.C5.

As an example, electrophoresis of fractions was carried out under non-reducing conditions in 4–15% gradient polyacrylamide gel. Samples were loaded in equal volumes containing comparable protein levels and ran for 40 min at 200 volts. After electrophoresis, the proteins in the gel were electrophoretically transferred to a polyvinylidene difluoride (PVDF) membrane. The transfer buffer contained 25 mM Tris, 192 mM glycine and 20% methanol at pH 8.3. The transfer was performed at 100 volts for one hour. After the transfer, the membrane was blocked for one hour in a broad function protein based blocker with gentle agitation. Such blockers include albumin, casein or dry milk solution. Such a blocker is commercially available as NAP-Sure blocker™

(Geno-Technology, Inc., St. Louis, Mo.). Immunostaining was carried out using 7E11.C5 antibody or monoclonal antibody to $\alpha_1$-antichymotrypsin at 5 μg/ml concentration diluted in NAP-Sure blocker™ (Geno-Technology, Inc., St. Louis, Mo.), for 1 hr. Secondary antibody, horse radish peroxidase conjugated goat anti-mouse IgG (Jackson Immuno Research Laboratories, Inc., West Grove, Pa.) at 1:5,000 dilution in 1% albumin/PBS/0.1% Tween 20, was incubated with the membrane for 45 min. The proteins were detected with enhanced luminol (ECL) reagent for horse radish peroxidase. Such a reagent is available under the trademark NEL 102, (NEN, Boston, Ma.). The complexed protein was then exposed to X-ray film to visualize the positive bands.

BRIEF DESCRIPTION OF THE DRAWINGS

FIG. 1 shows a Western-blot detection of PSMA in LNCaP cell extract and in prostate cancer patient after thiophilic gel chromatography. LNCaP cell extract or patient serum was chromatographed on 3-S-thiophilic gel. The presence of PSMA in column eluates was detected by SDS-PAGE and Western-blot using anti-PSMA antibody, 7E11.C5. "A" shows LNCaP cell extract and "B" shows prostate cancer patient serum (stage T-3). A total of four different preparations of LNCaP cell extracts and ten patient sera at stage $T_3$ were analyzed. The results in all cases were essentially identical.

FIG. 2 shows a Western-blot analysis indicating that PSMA in patient serum exists in the form of a complex between this antigen and $\alpha_1$-antichymotrypsin. Serum from stage $T_3$ prostate cancer patient was chromatographed on 3S, T-gel, analyzed by Western-blot and immunostained with anti-PSMA antibody, 7E11C5 (lane A) or anti $\alpha_1$-antichymotrypsin antibody (lane B). Two bands were detected by anti-ACT antibody; one corresponding $\alpha_1$ antichymotrypsin (lower band) and other to PSMA-ACT complex (upper band). The presence of PSMA-ACT complex was detected in 13 additional patients by similar procedure.

BRIEF DESCRIPTION OF THE INVENTION

Figure 3:
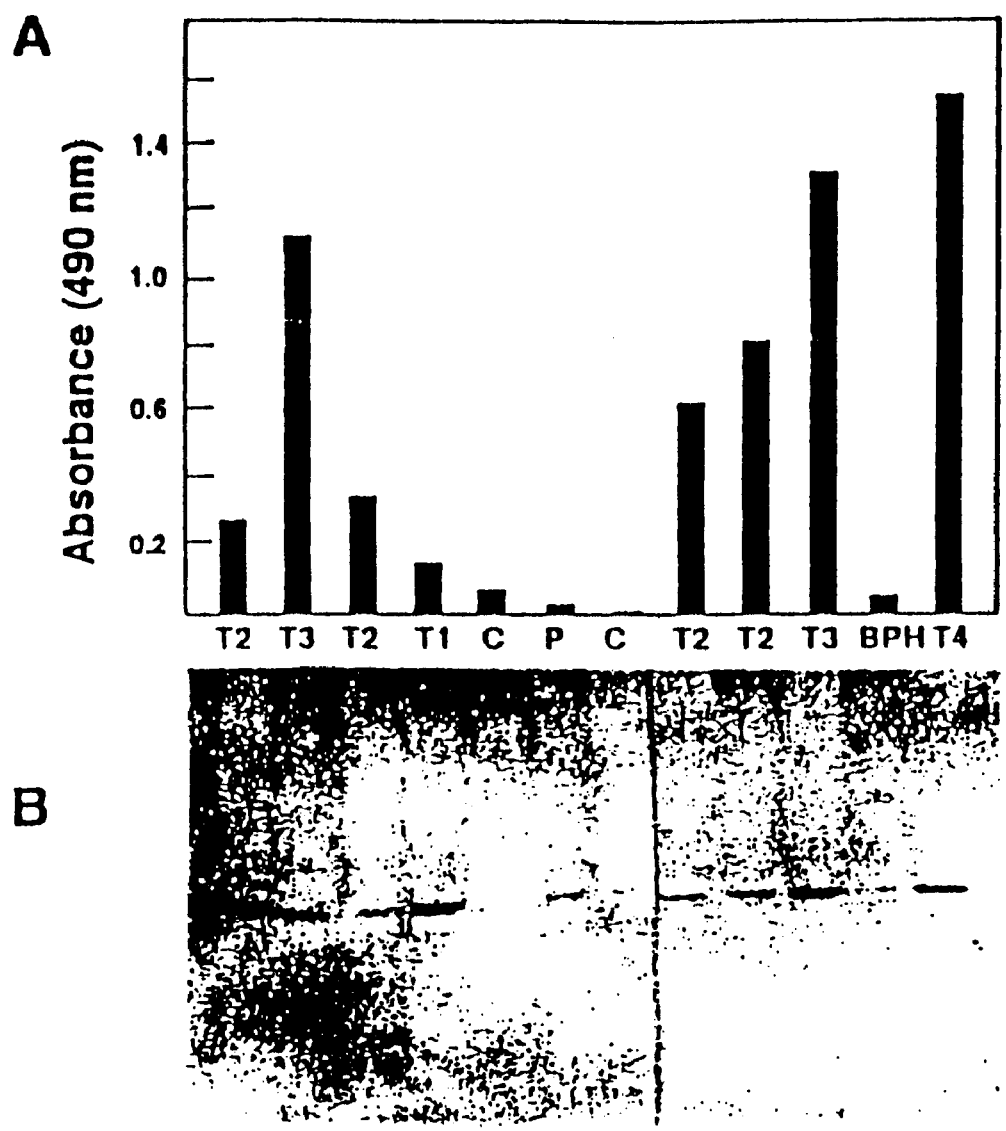
FIG. 3 shows a comparison of PSMA-ACT complex detection in sera of prostate cancer patients using sandwich ELISA (A) and Western-blot (B). PSMA was detected in each of the serum samples from $T_1$, $T_2$, $T_3$ and $T_4$ stage prostate cancer patients, C, controls, P, prostatitis and BPH. The data shown includes 12 representative serum samples at different stages of disease and controls.

The invention includes a method for detecting prostate specific membrane antigen (PSMA) in a body fluid sample containing PSMA by immunoassay including the steps of capturing PSMA from the sample using a PSMA antibody and detecting the captured PSMA with an anti-$\alpha_1$-antichymotrypsin antibody.

In a preferred embodiment, PSMA is captured using an appropriate dilution of anti-PSMA antibody, coating a surface such as the surface of wells in a microtiter plate, with the resulting solution, blocking non-specific sites on the surface with blocking solution such as albumin, diluting the sample with a blocking buffer such as buffered albumin and applying a diluted sample to the surface to capture PSMA. The body fluid is preferably serum but might be another fluid such as urine.

A preferred embodiment for detecting captured PSMA, includes the steps of removing non-captured material by washing the surface, applying anti-$\alpha_1$-antichymotrypsin antibody diluted in a blocking solution such as albumin solution and detecting bound PSMA using secondary antibody such as peroxidase labeled anti-rabbit IgG and a substrate such as O-phenylenediamine (OPD).

DETAILED DESCRIPTION OF THE INVENTION

"PSMA" as used herein is an antigen present in prostate tumor and in the membrane of LNCaP cells which complexes with $\alpha_1$ antichymotrypsin (ACT).

"Anti $\alpha_1$ antichymotrypsin antibody" (anti ACT antibody) is an antibody that specifically complexes with $\alpha_1$ antichymotrypsin.

"PSMA antibody" as used herein means an antibody that selectively captures PSMA. Examples of PSMA antibodies are 7E11.C5 (ATCC deposit no. HB-10494, U.S. Pat. No. 5,162,504) and B-6 (ATCC deposit no. PTA-3160).

"Blocking solution" is a solution containing a blocking compound having a wide variety of antigens used to block non-specific binding sites. The most common blocking solution is a solution of albumin, usually bovine serum albumin (BSA). Other blocking compounds such as milk solids, casein or mixed polysaccharides may be used to form a blocking solution.

"Blocking buffer" is a buffered blocking solution, the most common buffer is a phosphate buffer. Where blocking solutions are used in more than one step for detection by a particular antibody, the same blocking compound is usually present in the blocking solutions.

Serum samples from 55 prostate cancer patients, 9 samples from patients diagnosed with prostatitis, 46 samples from BPH patients and 20 serum samples from normal donors were processed through thiophilic adsorption chromatography that selectively retains PSMA. Isolated PSMA was analyzed by SDS-PAGE and Western blot using 7E11.C5 antibody.

It is essential that serum samples be processed through thiophilic gel chromatography prior to PSMA detection in a Western-blot analysis. However, in the case of PSMA determination by ELISA the thiophilic gel chromatography step is not required. PSMA can be monitored in the serum without any processing.

Double determinant ELISA was developed using PSMA antibody as a "capture" antibody for PSMA and polyclonal anti-$\alpha_1$-antichymotrypsin antibody as a "detection" antibody. ELISA results are expressed in arbitrary units derived from a standard curve based on dilution of pooled sera from three patients with advanced prostate cancer.

Results: PSMA has strong affinity for Thiophilic gel. Chromatography of patient serum on Thiophilic gel eliminates more than 90% of proteins including albumin, thus permitting the visualization in Western-blot analysis of PSMA as a single band corresponding to ~75 to 90 kDa when stained with the PSMA antibody. The staining was more intense with the sera of prostate cancer patients as compared to non-cancerous sera (normal, prostatitis and BPH). PSMA isolated from the prostate cancer cell line, LNCaP and processed identically also showed a single band but with a somewhat higher molecular weight corresponding to 100 to 110 kDa. A direct, sandwich enzyme-linked immunosorbent assay (ELISA) was developed for the determination of serum PSMA. In ELISA, PSMA levels are expressed as arbitrary units and the results correlate well to the stage of the disease.

Preparation of LNCaP Cell Extract

LNCaP cells were obtained from the American Type Culture Collection (ATCC deposit number CRL1740, Rockville, Md.). These cells were originally isolated and characterized at Roswell Park Cancer Institute, Buffalo, N.Y. Details regarding the development and characterizations of the cell line have been published by Horoszewicz, et al., LNCaP model of prostatic carcinoma, Cancer Res, vol 43, pp 1809–1818, 1983.

The LNCaP cells were maintained in complete RPMI 1640 growth medium as published by G. Moore, et al., AMA, V. 199, pp. 519, 1967) supplemented with 10% fetal bovine serum and 1 mM L-glutamine. Confluent monolayers of LNCaP cells were trypsinized, washed with PBS, and the cell suspension was frozen at −70° C. in the presence of 1 µg/ml of protease inhibitor (Aprotinin, Sigma Chemical Co., St. Louis, Mo.). After one additional cycle of freezing and thawing, the cell lysate was centrifuged at 3,000×g to remove the nuclei and incompletely disrupted cells. The supernatant was reconstituted to contain 0.5% NP40 and placed on the rotary shaker for 30 min at 4° C. The solubilized material was spun at 15,000×g for 30 min. the supernatant was collected and stored at −70° C. until used.

Serum Samples

Serum samples from 110 patients (prostatitis, BPH and prostatic carcinoma) and 20 healthy donors were used in this study. Among the patients, 37 blood samples were freshly drawn during routine outpatient visits in the clinic and 18 patient serum samples were obtained as archived serum samples from the Department of Laboratory Medicine at Roswell Park Cancer Institute. The remaining 54 patient serum samples were freshly drawn from patients during routine visits to urology clinics in the Western New York area. All serum samples were kept frozen at −70° C. and processed within 72 hours with the exception of archived samples that were analyzed within 90 days of collection. All donors including normal healthy individuals gave written informed consent as per local regulatory requirements. Serum samples were kept frozen at −70° C. until used.

Antibody

7E11.C5 hybridoma cell line (ATCC—HB-10494) and B-6 hybridoma cell line (ATCC—PTA 3160) are routinely maintained in our laboratory and have been deposited in and are available from the American Type Culture Collection. 7E11.C5 antibody and B-6 antibody were purified from mouse ascites by affinity chromatography using Protein-A coupled to crosslinked agarose beads via chemically stable amide bonds e.g., (Affi-Gel Protein-A MAPS II system, Bio-Rad, laboratories, Hercules, Calif.) according to published manufacturer's instructions. Monoclonal antibodies 7E11.C5 and B-6 are a murine immunoglobulin (IgG1) generated by immunization with LNCaP cells. These antibodies react with membrane rich fractions of LNCaP cells, but have no reactivity with cytosol or antigenic substances such as prostate-specific antigen (PSA) or Prostatic acid phosphatase (PAP).

PSMA-Quantitation by Double-determinant ELISA

PSMA quantification in unprocessed serum samples was carried out as follows: Monoclonal antibody 7E11.C5 was diluted to 5 µg/ml in 20 mM phosphate buffer saline, pH 7.0 PBS and used for coating the wells in a microtiter plate overnight at 4° C. The wells were blocked with 2% bovine albumin in PBS blocking buffer for one hour. The blocking and all subsequent steps were carried out at room temperature. Test samples were diluted with blocking buffer and applied to the plate in triplicate (50 µl/well). After one hour of incubation, the plates were washed with PBS and $\alpha_1$-antichymotrypsin polyclonal antibody at 1:2000 dilution in 1% albumin in PBS0.1%/Tween 20 (50 µl/well) was applied. Bound antigen was detected by peroxidase-labeled anti-rabbit IgG and O-phenylenediamine (OPD) substrate. A pooled serum from $T_3$ stage cancer patients was used as an internal standard, and results are expressed in arbitrary units derived from a standard curve run on each plate.

Results

Figure 1:
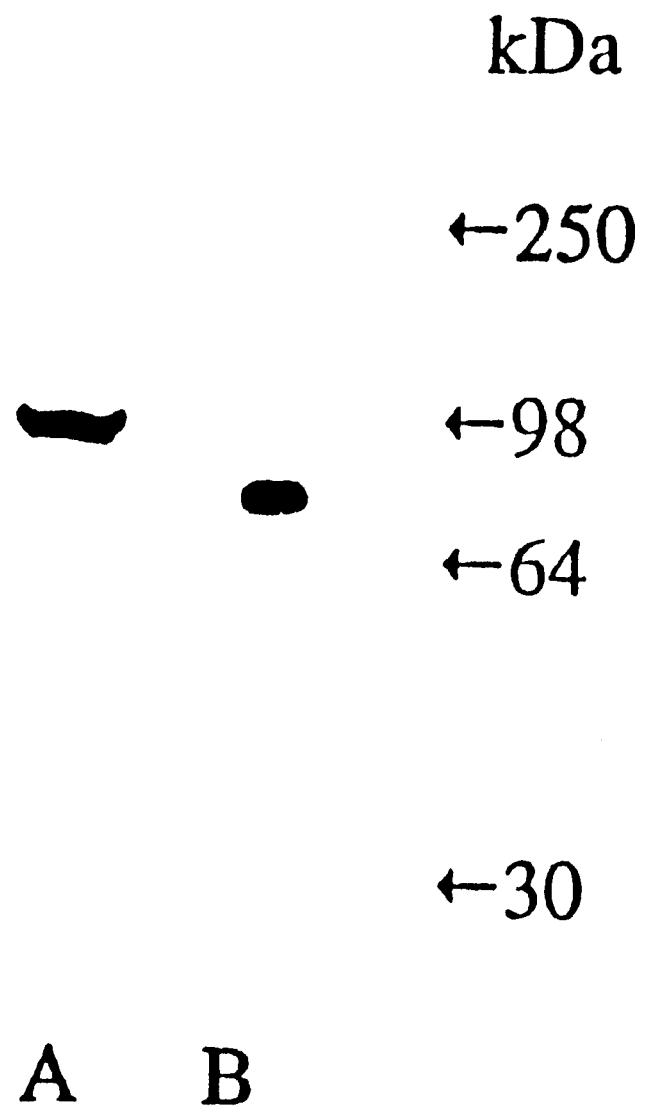

Detection of PSMA in LNCaP Cell Extract and in Prostate Cancer Patient Serum by Western-blot In a separate series of experiments, we have shown that PSMA has strong affinity for 3S-thiophilic gel. LNCaP cell extract (1 ml; 5×10$^7$ cells) or serum (400 µl) from prostate cancer patient was chromatographed on 3S, T-gel as described earlier. Ten microliters of eluted fractions were subjected to SDS PAGE/Western-blot analysis and immunostained with the 7E11.C5 antibody. In case of LNCaP cell extract, it was necessary to concentrate the eluted fractions (6×) prior to SDS-PAGE analysis. Column eluates from thiophilic gel chromatography were analyzed immediately without any freezing. Results of one such experiment are shown in FIG. 1. Only one band of immunoreactivity corresponding to 75–90 kDa (serum) or 100–110 kDa (LNCaP cell extract) was seen among various samples. In all cases PSMA recovered from patient serum is always lower in molecular weight in comparison to PSMA in LNCaP cells. However, column eluates of LNCaP cell extract, after a few freeze and thaw cycles often showed a second faint PSMA band corresponding to 180 kDa. This 180 kDa band has been observed by others, e.g. Troyer, et al. supra. Thiophilic gel chromatography evidently removes many proteins in the serum that allows PSMA detection, after electrophoretic separation and transfer to PVDF membranes, when stained with anti-PSMA antibody. No immunoreactivity was seen when 7E11.C5 antibody was used to stain Western-blots of patients' serum prior to thiophilic gel chromatography.

Figure 2:
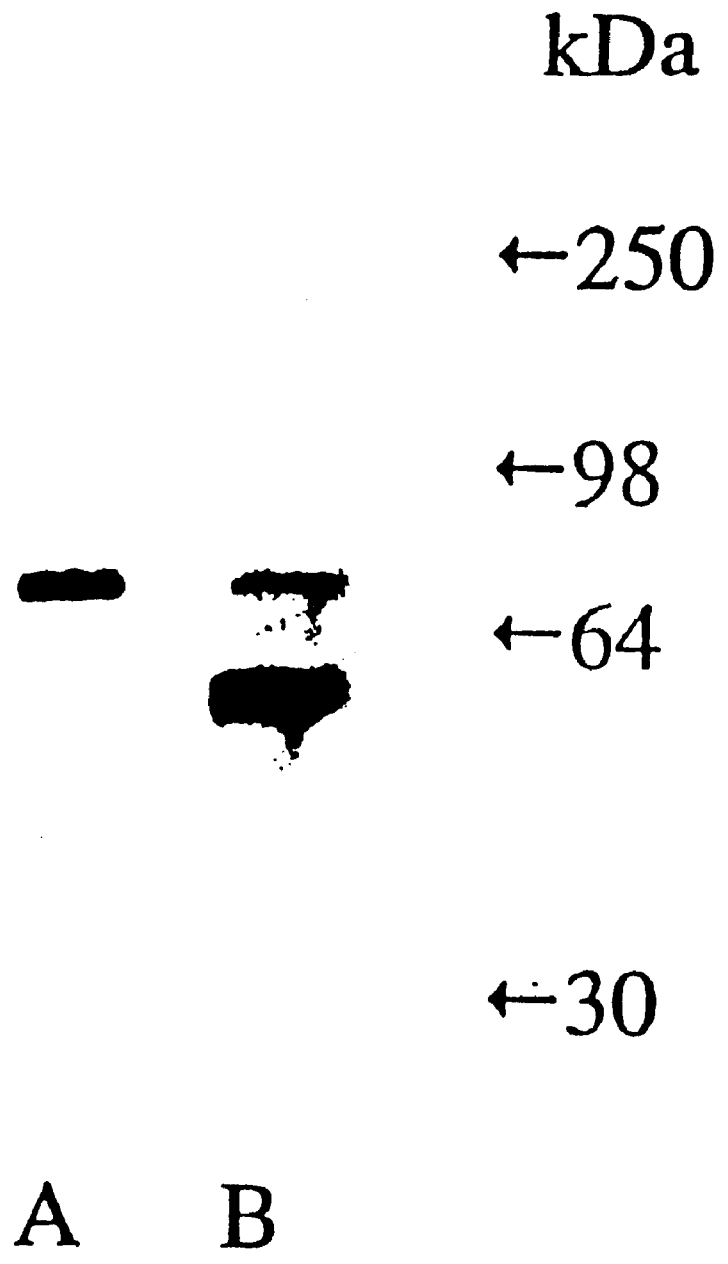

The molecular weight of PSMA varies depending upon its origin: PSMA in LNCaP cell extracts has a molecular weight of 100–110 kDa (Israeli, et al. supra; and Troyer, et al. supra); PSMA isolated from prostate cancer tumor tissue is 120 kDa (Troyer, et al. supra). In our studies, we have observed that PSMA in the sera of different prostate cancer patients has a molecular weight of approximately 75–90 kDa (FIG. 1). The reasons for these differences are not known. PSA is known to complex with different protease inhibitors (Polascik, et al. supra) It is conceivable that PSMA also complexes with different proteins/protease inhibitors. In our studies, we have explored such a possibility. Sera from prostate cancer patients, at different stages of the disease, were initially processed through thiophilic gel adsorption chromatography, and analyzed by SDS-PAGE/Western-blot. After electroblotting, membranes were stained with anti-PSMA antibody, 7E11.C5 or with monoclonal antibodies to protease inhibitors such as $\alpha_1$-antitrypsin, $\alpha_1$-antichymotrypsin and Protein-C inhibitor. Data presented in FIG. 2A shows one band of immunoreactivity with 7E11.C5 antibody. No immunoreactivity was seen with antibodies to $\alpha_1$-antitrypsin or Protein-C inhibitor. Two bands of immunoreactivity were seen with antibody to $\alpha_1$-antichymotrypsin; one corresponding to PSMA/$\alpha_1$-antichymotrypsin complex and other corresponding to free $\alpha_1$-antichymotrypsin, known to be present in the serum (FIG. 2B). In our earlier studies (data not shown) we have documented that free $\alpha_1$-antichymotrypsin has an affinity for thiophilic gel.

This is the first evidence that PSMA in the serum exists as a complex with $\alpha_1$-antichymotrypsin (PSMA-ACT). Attempts to make such a complex by incubating PSMA preparations from LNCaP cells with female serum or with commercially available $\alpha_1$-antichymotrypsin were unsuccessful.

Figure 4:
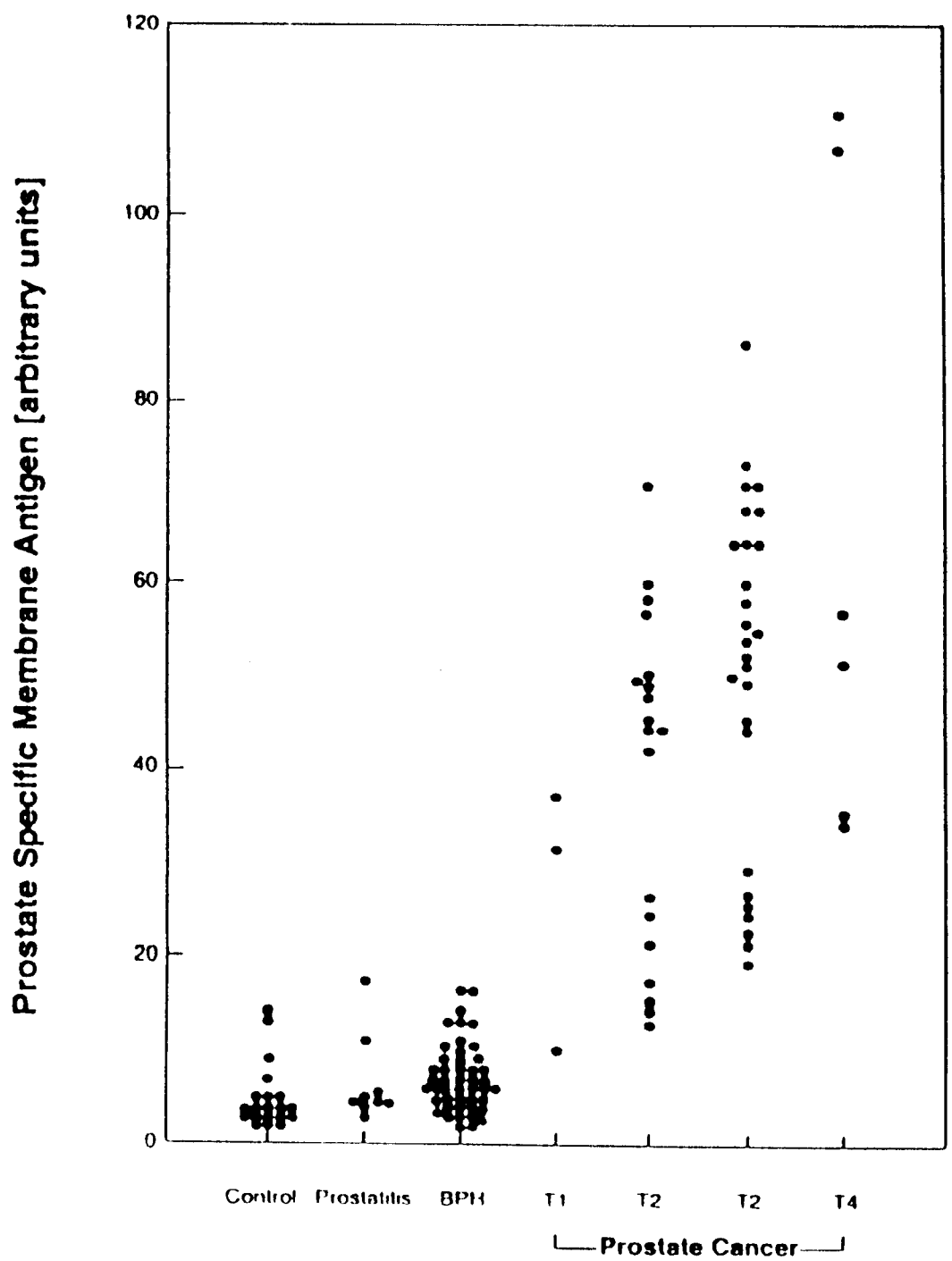
FIG. 4 shows a graph of ELISA determination of PSMA-ACT complex in patient sera. A total of 130 serum samples including normal control (20), prostatitis (9), BPH (46) and different stages of prostate cancer (55), were analyzed by sandwich ELISA. The antigen was captured by monoclonal anti-PSMA antibody, 7E11.C5 and detected by polyclonal anti-ACT antibody. The results are expressed as arbitrary units derived from a standard curve included in each microplate. The standard consists of a serial, two-fold dilution of pooled serum from T-3 stage patients spanning the range from one unit (1:160 dilution) to 100 units (1:5 dilution). Each dot represents one serum sample. The graph shows very little overlap at about 10 units with non-prostate cancer samples generally falling below ten and prostate cancer samples falling above 10.
Figure 5:
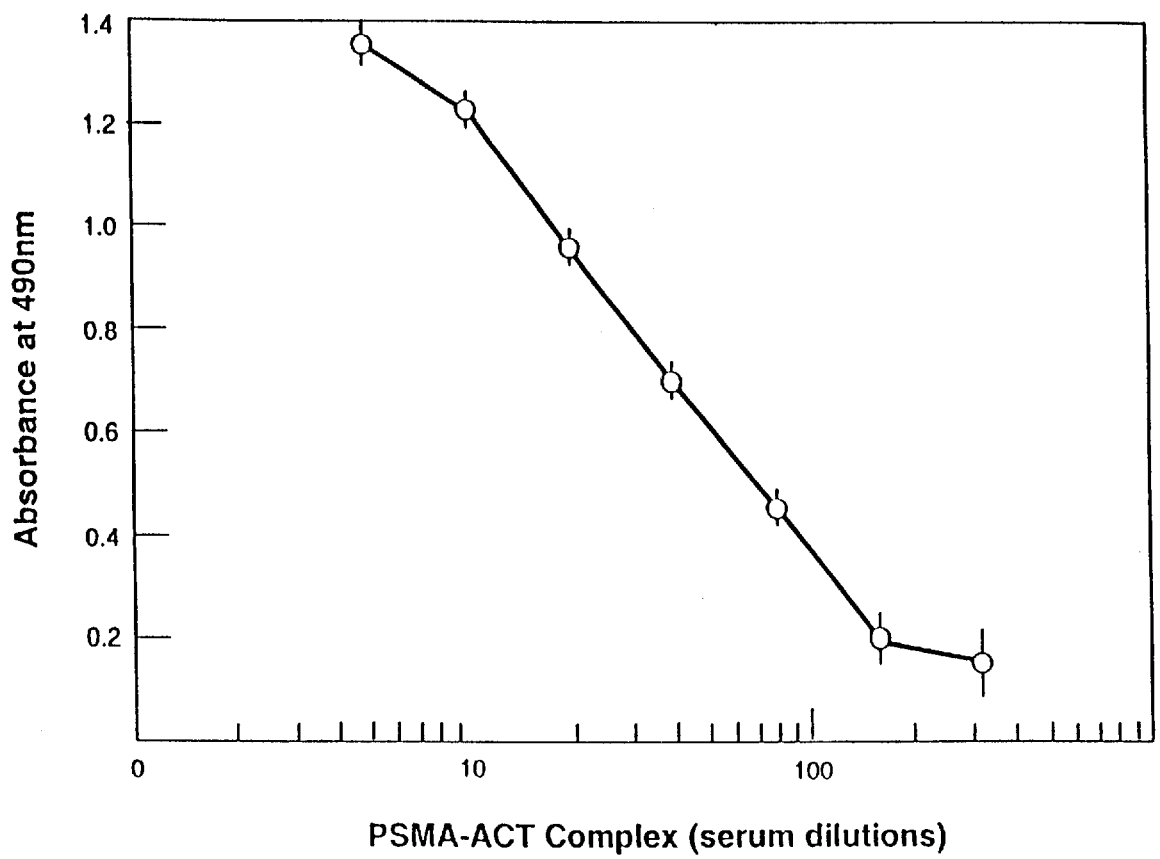
FIG. 5 shows calibration of the ELISA for PSMA-ACT complex. Pooled serum sample from three T-3 stage prostate cancer patients was diluted serially and 50 μl aliquots added to microtiter plates, in triplicate, coated with anti-PSMA antibody. Anti-ACT antibody was used to detect the presence of PSMA-ACT complex. Normal serum at comparable dilution was used as a control The standard consists of a serial dilution of pooled serum spanning the range from one unit (1:160 dilution) to 100 units (1:5 dilution). The results shown here represent six independent assays.

Detection of PSMA-ACT Complex in Prostate Cancer Patients Serum by Western-blot and ELISA Sera from 55 prostate cancer patients at different stages of the disease, along with some normal (20), BPH (46) and prostatitis (9) serum samples were randomized in a blind fashion and analyzed for the presence of PSMA. All serum samples were subjected initially to thiophilic gel chromatography. The column eluates were analyzed for the presence of PSMA by SDS/PAGE/Western-blot analysis and immunostained with 7E11.C5 antibody. Data presented in FIG. 3A represents one or each of: control, BPH, prostatitis serum and sera from 8 prostate cancer patients at different stages of the disease ($T_1$, $T_2$, $T_3$, and $T_4$). In all cases, only one band of immunoreactivity corresponding to 75–90 kDa was seen. The intensity of immunostaining was significantly higher in sera from cancer patients as compared to non-cancerous patients. Similar results are found using anti-PSMA antibody B-6, see FIG. 6. We have documented in FIGS. 2 and 6, that PSMA-ACT complex in patient serum can be identified with PSMA antibody and anti $\alpha_1$-antichymotrypsin antibody. This observation, for the first time, provided an opportunity to develop an ELISA assay for monitoring the PSMA in patient serum by using PSMA antibody, e.g., 7E11.C5 or B-6, as a "capture" antibody, and anti-$\alpha_1$-antichymotrypsin antibody as a "detection" antibody. All serum samples, as indicated in FIG. 3B, were analyzed for the presence of PSMA-ACT complex in sandwich ELISA. The ELISA results as shown in FIG. 3A, are expressed as absorbence at 490 nM. As can be seen, the levels of PSMA-ACT in BPH or prostatitis are low as compared to more advanced disease. The levels of PSMA as detected by Western-blot analysis (FIG. 3 at B), correspond to what can be seen in sandwich ELISA (FIG. 3 at A). Since PSMA-ACT complex can be detected in the serum and the fact that there is no serum based PSMA preparation available as yet, we have used a pooled serum from three prostate cancer patients ($T_3$ Stage) to prepare internal standards to be used for screening of the sera. We obtained a linear dose response curve with serum dilutions ranging from 1:5 to 1:160. (FIG. 5) A total of 130 serum samples were assayed for PSMA-ACT complex levels in this newly developed sandwich ELISA and results are presented in FIG. 4. PSMA results are expressed in arbitrary units which were derived from a standard curve run on each plate. PSMA levels in controls, BPH and prostatitis are usually less than 10 units; whereas PSMA levels are higher at different stages of the disease and usually correlate well with disease progression. These results are far superior to the current PSA test where false positives routinely exceed true positives.

B-6 hybridoma clone was originally isolated from uncloned culture of 7E11 hybridoma cells which is also the parental source of 7E11.C5 cells. B-6 hybridoma cells were expended in RPMI 1640 medium containing 10% heat inactivated fetal bovine serum. B-6 hybridoma cells were cryopreserved.

The ability of B-6 hybridoma cells to produce antibody that selectively identifies prostate specific membrane antigen was confirmed by three different methods: (a) indirect immunoperoxidase staining; (b) Western-blot and (c) sandwich ELISA. Conditioned medium from B-6 cells containing antibody to PSMA was used for immunostaining of prostate cancer cells. B-6 cells were used to produce ascities in Balb/c mice and purified antibody was used for ELISA and Western-blot analysis.

Monoclonal Antibody Production and Purification

Balb/c mice, 6–8 weeks old, were injected intraperitonially with B-6 cells ($5 \times 10^6$ cells/mouse in 0.5 ml of PBS). Three weeks later ascites were harvested and monoclonal antibody (B-6) was purified first by precipitation with ammonium sulfate followed by Protein-A agarose column chromatography as per manufacturer's instructions. The purity of IgG was confirmed by SDS/PAGE and Coomassie-blue staining. IgG concentration was measured by BCA assay method (Pierce, Rockford, Ill.).

Indirect Immunoperoxidase Staining

For immunostaining, four human prostate cancer cell lines (PC-3, PC-3M, DU-145, LNCaP) and two lines of normal human fibroblast cells (BG-9, MLD), were used. Freshly prepared cytospin smears of cultured cells, unfixed and formalin fixed, were first treated for 1 hour with a blocking solution (1% albumin in PBS) and subsequently incubated for 1 hour with B-6 conditioned medium (1:500 dil in blocking solution) that contains B-6 antibody. After washing the cells three times with PBS, they were exposed to peroxides conjugated goat-anti-mouse IgG (Jackson Immune Research Laboratories) at 1:10,000 dilution for 60 min. The color reaction was developed with 3,3'-diaminobenzidine (0.05%):$H_2O_2$ (0.01%) in PBS, pH 7.2. PBS in place of primary antibody and culture fluid from myeloma cell line were included as additional controls. The intensity of immunospecific staining was evaluated using Zeiss microscope (40× objective; 10× occular).

None of the unfixed cell lines showed any immunoreactivity to B-6 antibody. Among the cells fixed with formalin, only LNCaP cells showed specific immunoreactivity to B-6 antibody. The intensity of immunoperoxidase staining of LNCaP cells is predominantly in trans-membrane region. No such immunoreactivity was seen with fixed PC-3, PC-3M, DU-145, BG-9 and MLD cells.

Western-blot Analysis

Cell lysate from LNCaP, PC3 and DU-145 were used for Western-blot analysis using B-6 antibody. Cells were trypsinized, washed with PBS and subjected to two freeze and thaw cycles. The cell lysate was centrifuged at 2,000×g for 10 min and supernatant was incubated for 30 min at 4° C. after addition of NP-40 (0.5% final concentration). The solubilized material was spun at 10,000×g for 20 min and supernatant was used for 3S, T-gel chromatography as described earlier. The fractions from the T-gel column containing PSMA were pooled, concentrated (×6) and applied to 4–15% SDS/PAGE under nonreducing conditions. After electrophoretic transfer to PVDF membrane, PSMA antigen was identified by B-6 antibody.

Figure 6:
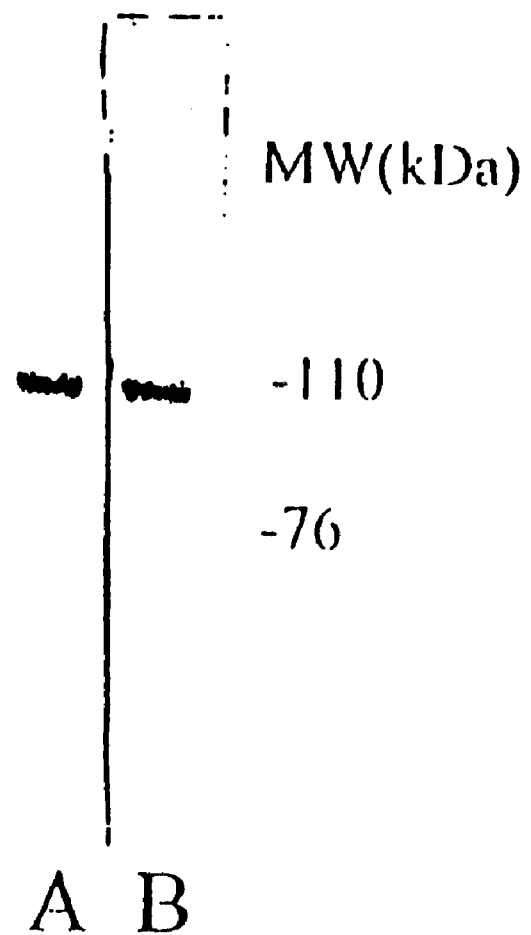
FIG. 6 shows detection of PSMA in LNCaP cell lysate by isolation by thiophilic gel chromatography followed by Western-blot analysis using (A) 7E11.C5 antibody and (B) B-6 antibody.

Cell lysate from DU-145 and PC-3 cells did not show any immunoreactivity with B-6 antibody. However, a single immunoreactive band corresponding to 100–110 kDa was seen in case of LNCaP cell preparation. In a separate experiment LNCaP cell lysate was probed in parallel with both B-6 and 7E11.C5 antibodies. The results are shown in FIG. 6. Both antibodies were able to identify PSMA antigen in LNCaP cell lysate.

ELISA

Figure 7:
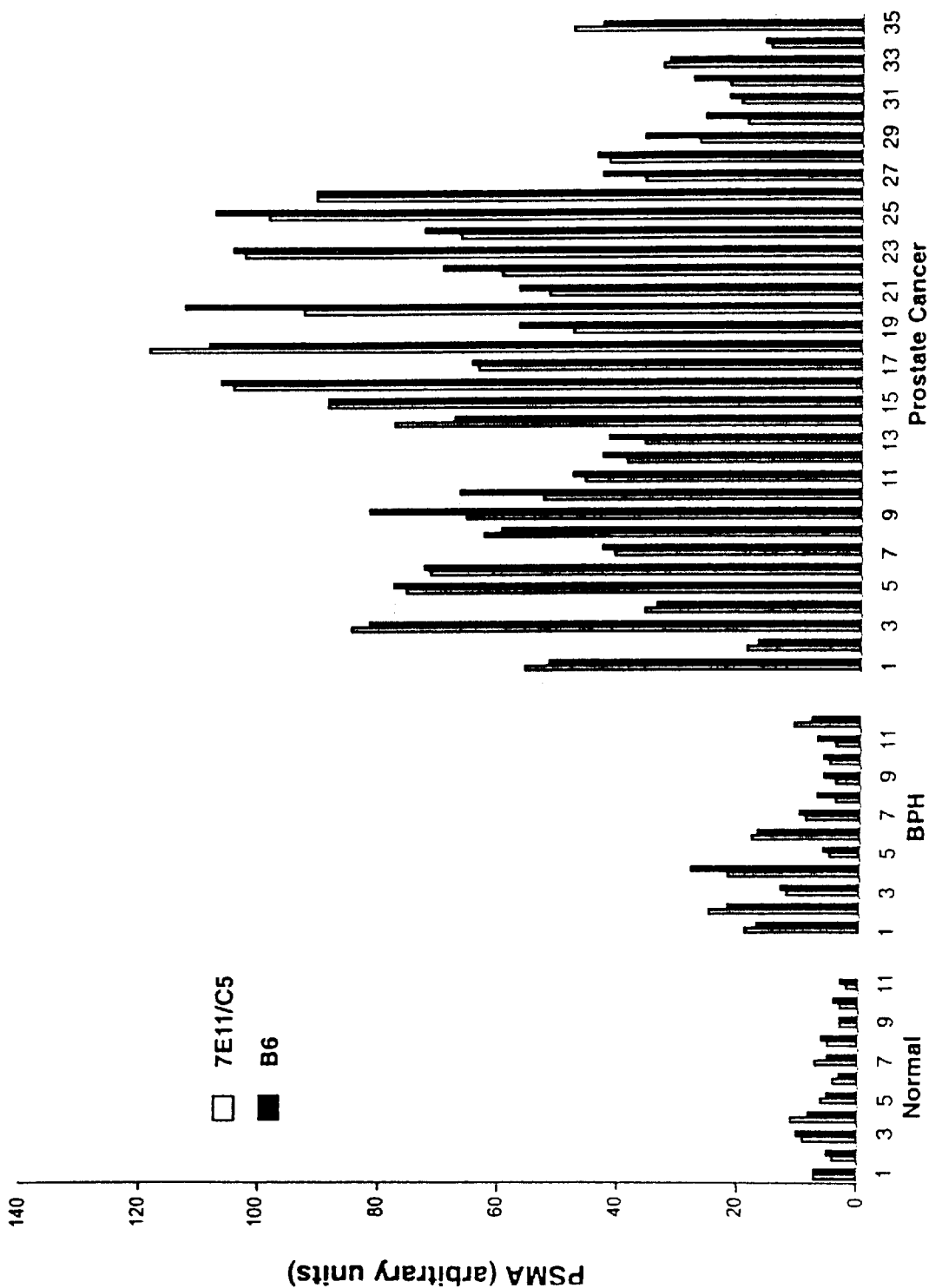
FIG. 7 shows comparison of 7E11.C5 and B-6 antibodies to measure PSMA-ACT complex in the sera of prostate cancer patients by ELISA. A total of 58 serum samples including normal controls (11), BPH (12) and prostate cancer patients (35) were analyzed by sandwich ELISA. The antigen was captured either by monoclonal 7E11.C5 or monoclonal B-6 antibody and detected by polyclonal anti-ACT antibody. The other details are as described before. The results are expressed as arbitrary units.

B-6 and 7E11.C5 antibodies were used to measure PSMA in the serum of prostate cancer patients by ELISA assay. Sera from normal individuals and patients with BPH were also included. Ninety six well immunoplates were divided in two equal halves; one half for coating with B-6 antibody and the other half for coating with 7E11.C5 antibody. Each half of the plate had its own internal standard for PSMA. The other details of ELISA procedure are similar to those described earlier. The results of this test are shown in FIG. 7. For each serum, the index of PSMA antigen is essentially identical with both B-6 and 7E11.C5 antibodies.

Based upon the results of ELISA and Western-blot analysis, it is clear that both B-6 and 7E11.C5 antibodies can be effectively utilized to detect the presence of PSMA in the sera of prostate cancer patients. The level of PSMA in cancer patients is significantly higher as compared to BPH or Prostatitis.

We have monitored serum PSMA levels both by ELISA and by Western-blot analysis. For Western-blot analysis, the serum was chromatographed on 3S-thiophilic gel that eliminated a majority of the serum proteins. Serum, after thiophilic gel processing, was analyzed by SDS-PAGE and Western-blot using PSMA antibody. In all cases, a single PSMA-band corresponding to 75 to 90 kDa was seen. A total of 130 serum samples were processed. A representative result including prostate cancer patient sera, BPH, prostatitis and normal sera are shown in FIG. 3B. It is worthy of mention that the molecular weight of PSMA present in the serum and in extracts of LNCaP cells are different. Serum PSMA is 75–90 kDa, whereas PSMA from LNCaP cells is 100–110 kDa. The molecular weight of PSMA from LNCaP cells remained the same both, under reducing or non-reducing conditions. However, under reducing conditions, PSMA from the serum is undetectable in Western-blot. Since additional antibodies to PSMA are now available (Liu, et al. supra; and Grauer, et al. supra), attempts have been made to develop immunoassay to monitor PSMA levels in different body fluids. Sokoloff, et al., have developed a dual-monoclonal sandwich assay for PSMA (Sokoloff, et al., A dual-monoclonal sandwich assay for prostate-specific membrane antigen: Levels in tissues, seminal fluid and urine, Prostate, vol 43, pp 150–157, 2000). They were successful in measuring PSMA levels in tissue extracts, in urine and in seminal fluid. However, their attempts to monitor PSMA levels in the serum were unsuccessful. Our attempts to monitor PSMA levels in the serum were successful. This success was largely due to the recognition, for the first time, that PSMA in the serum exists as a complex, with $\alpha_1$-antichymotrypsin (PSMA-ACT). In our sandwich ELISA, we have used a PSMA antibody 7E11.C5 and B-6 as "capture" antibodies and an anti $\alpha_1$-antichymotrypsin antibody as the "detection" antibody.

It is known that PSMA is a transmembrane glycoprotein. It is also known that a PSMA antibody binds only to $NH_2$-terminus of PSMA. PSMA, as detected in the serum, must be a fragment of this antigen containing epitope for PSMA and when it complexes with ACT, it attains the molecular weight of 75–90 kDa.

PSMA detection in Western-blot analysis was feasible only after LNCaP cell extracts were processed through thiophilic gel chromatography that effectively eliminated the majority of interfering proteins. Molecular weights of PSMA in extracts of LNCaP cells and in the serum are different. Serum PSMA is 75–90 kDa whereas PSMA in LNCaP cells is 100–110 kDa. For the first time, serum PSMA can be detected by sandwich ELISA. Evidently, a fragment of PSMA containing an epitope for 7E11.C5 or B6 antibody is released into the serum that complexes with $\alpha_1$-antichymotrypsin to form a PSMA-ACT complex. This constitutes the basis for the newly developed ELISA test. In our ELISA test the 7E11.C5 or B6 antibody was used to capture PSMA and detection was based upon the use of $\alpha_1$-antichymotrypsin antibody. The level of PSMA as detected by ELISA correlates well with the stage of the disease.

What is claimed is:

1. A method for detecting prostate specific membrane antigen (PSMA) in a body fluid by immunoassay which comprises capturing PSMA from a body fluid sample containing PSMA, using a PSMA antibody and detecting the captured PSMA with an anti-$\alpha_1$-antichymotrypsin antibody.

2. The method of claim 1 wherein PSMA is captured using a PSMA antibody by diluting the PSMA antibody; coating a surface with the resulting solution; blocking non-specific sites on the surface, diluting the sample with a blocking buffer and applying a diluted sample to the wells to capture PSMA.

3. The method of claim 1 where the body fluid is serum.

4. The method of claim 1 where the body fluid is urine.

5. The method of claim 2 wherein captured PSMA is detected with anti-$\alpha_1$-antichymotrypsin antibody by washing the wells to remove non-captured material; applying anti-$\alpha_1$-antichymotrypsin antibody diluted in blocking solution and detecting bound PSMA using peroxidase labeled anti-rabbit IgG and OPD substrate.

6. The method of claim 2 where the body fluid is serum.

7. The method of claim 2 where the body fluid is urine.

8. The method of claim 5 where the body fluid is serum.

9. The method of claim 5 where the body fluid is urine.

* * * * *